United States Patent [19]

Kerschner et al.

[11] Patent Number: 5,175,333

[45] Date of Patent: Dec. 29, 1992

[54] TRANSESTERIFICATION ROUTE TO QUATERNARY AMMONIUM SUBSTITUTED CARBONATE ESTERS

[75] Inventors: Judith L. Kerschner, Hawthorne; Sharon M. Jureller, Little Ferry; Charles C. Nunn, Rutherford, all of N.J.

[73] Assignee: Lever Brothers Company, Division of Conopco, Inc., New York, N.Y.

[21] Appl. No.: 827,847

[22] Filed: Jan. 29, 1992

Related U.S. Application Data

[63] Continuation of Ser. No. 582,282, Sep. 14, 1990, abandoned.

[51] Int. Cl.$^5$ .............................................. C07C 69/96
[52] U.S. Cl. ...................... 558/271; 558/265; 558/268; 558/273; 558/276
[58] Field of Search ............... 558/265, 266, 268, 269, 558/270, 273, 274, 276

[56] References Cited

U.S. PATENT DOCUMENTS

| | | | |
|---|---|---|---|
| 4,410,464 | 10/1983 | Hallgren | 558/271 |
| 4,440,692 | 4/1984 | Kalbacher et al. | 558/271 X |
| 4,545,999 | 10/1985 | Riemer et al. | 558/271 X |
| 4,546,000 | 10/1985 | Zanno et al. | 558/271 X |
| 4,994,594 | 2/1991 | Silva et al. | 558/268 |

Primary Examiner—Arthur C. Prescott
Attorney, Agent, or Firm—Milton L. Honig

[57] ABSTRACT

A process is reported for preparation of quaternary ammonium type carbonate esters which are useful as bleach precursors in detergent compositions. The process involves transesterification of low molecular weight carbonates, e.g. diphenyl carbonate, with amino functionalized alcohols, e.g. dialkylaminoalkanol. Preferably the reaction involves transesterification of diphenylcarbonate with the hydroxyl compound followed by removal of phenol. Subsequent thereto the transesterified ester is quaternized with an alkylating agent. Optionally there may be a sulfonation of phenol ester subsequent to the quaternization reaction.

14 Claims, No Drawings

TRANSESTERIFICATION ROUTE TO QUATERNARY AMMONIUM SUBSTITUTED CARBONATE ESTERS

This is a continuation application of Ser. No. 07/582,282 filed Sep. 14, 1990, now abandoned.

BACKGROUND OF THE INVENTION

1. Field of the Invention

The invention relates to a process for preparing quaternary ammonium substituted carbonate esters useful as bleach precursors in detergent compositions.

2. The Related Art

Peroxygen compounds such as sodium perborate are ineffective at bleaching fabrics under wash-water temperatures below 60° C. Good low temperature performance can however be achieved through combination of the peroxygen compound with a precursor as activating agent.

A recently issued patent, U.S. Pat. No. 4,751,015 (Humphreys et al), reported an unusually effective family of bleach precursors identified as quaternary ammonium substituted peroxy carbonic acid esters. Various synthetic routes have been proposed to obtain these materials.

One route involves the reaction of an alcohol such as cholyl chloride with phosgene in an aprotic organic solvent to form a hydrogen chloride complex of a cholyl chloroformate. Subsequent thereto, the chloroformate is combined with a second hydroxylic material such as phenol sulfonate. See U.S. Pat. No. 4,988,817.

Another synthetic avenue is described in U.S. Pat. No. 4,985,561. Therein is reported the reaction of an aryl chloroformate with sulfur trioxide forming an aryl sulfonated chloroformate. This intermediate is then condensed with a quaternary ammonium substituted alcohol such as cholyl chloride.

There are several problems with the aforementioned synthetic schemes. Both require phosgene chemistry and the concomitant elimination of hydrogen chloride during the esterification steps. Hydrogen chloride is highly corrosive to equipment. Capital expense is therefore significantly increased. Pollution problems also arise with the generation of acid by-products. The phosgene route also forms considerable quantities of sodium chloride which are not easily removable from the desired products. Sodium chloride is hygroscopic and adversely impacts upon stability of the desired carbonate esters.

Transesterification has been proposed as a route to obtain carbonate esters. U.S. Patent 2,691,017 (Dornfeld) reports syntheses of bis-aminoalkyl carbonate derivatives through transesterification of diethylcarbonate with alkylamino compounds followed by quaternization of the amine group. From this reference there is no indication that an asymmetric displacement with aminoalkanol onto the reactant carbonate would be achievable. There is also no teaching as to how a sulfophenol ester could be formed through this transesterification route.

A still further method of achieving quaternary ammonium substituted carbonate esters is reported in a concurrently filed U.S. application Ser. No. 582,278. Therein is disclosed transesterification of low molecular weight carbonates, e.g. diphenyl carbonate, with quaternary ammonium functionalized alcohols, e.g. choline chloride. The problem with that route is that only a small percentage of the asymmetric carbonate is formed; the major product is the symmetrical bis-substituted quaternary ammonium functionalized carbonate ester.

Accordingly, it is an object of the present invention to provide an improved synthesis of quaternary ammonium type carbonate esters.

A more specific object of the present invention is to provide a route to quaternary ammonium type carbonate esters not involving generation of any hydrogen chloride by-products.

A still further object of the present invention is to provide a synthetic route to quaternary ammonium type carbonate esters through an environmentally friendly procedure and wherein good yields are achievable of asymmetrically substituted carbonate esters.

These and other objects of the present invention will become more readily apparent upon consideration of the detailed description and examples which follow.

SUMMARY OF THE INVENTION

A process is provided for the preparation of quaternary ammonium carbonate esters of the formula:

$$A-O-\overset{O}{\underset{\|}{C}}-O-B \quad (I)$$

wherein:
A is Z$^-$ 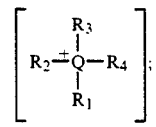

$R_1$, $R_2$ and $R_3$ are each a radical selected from the group consisting of alkyl, alkenyl, alkynyl, cycloalkyl, cycloalkenyl, aryl, $R_4OC(O)OL$;

or $R_1$ and $R_2$ together form an alkyl substituted or unsubstituted nitrogen-containing heterocyclic ring system;

or at least one of $R_1$ and $R_2$ is attached to $R_4$ to form an alkyl substituted or unsubstituted nitrogen-containing heterocyclic ring system;

$R_4$ is selected from a bridging group consisting of alkylene, cycloalkylene, alkylenephenylene, arylene, and polyalkoxylene, and wherein the bridging group can be unsubstituted or substituted with $C_1-C_{20}$ atoms selected from alkyl, alkenyl, benzyl, and aryl radicals;

$Z^-$ is a monovalent or multivalent anion leading to charge neutrality when combined with $Q^+$ in the appropriate ratio and wherein $Z^-$ is sufficiently oxidatively stable not to interfere significantly with bleaching by a peroxy carbonic acid;

Q is nitrogen or phosphorus;

B is $R_1$ or L; and

L is selected from the group consisting of:

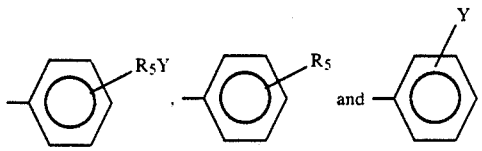

wherein $R_5$ is a $C_1-C_{12}$ alkyl group, and Y is H or a water solubilizing unit selected from the group consisting of $-SO_3^-M^+$, $-COO^-M^+$, $-SO_2^-M^+$, $-N^+(R_5)_3X^-$, $-NO_2$, $-OH$, and $-N(O)(R_5)_2$ and mixtures thereof; $M^+$ is a cation which provides solubility to the ester, and $X^-$ is an anion which provides solubility to the ester;
comprising the steps of:
(i) forming an ester by transesterifying a hydroxyl compound of the formula:

with $R_8OC(O)OR_8$ wherein $R_8$ is a substituted or unsubstituted phenyl, $C_1-C_{20}$ alkyl, and mixtures of radicals thereof; and (ii) reacting the transesterified ester with $R_3Z$ to form the quaternary ammonium carbonate ester, $R_3$ being a $C_1-C_4$ alkyl group and Z being the same as $Z^-$ except without charge.

Advantageously, the $R_8OC(O)OR_8$ is diphenyl carbonate and transesterification is conducted in the absence of any solvent, with the diphenyl carbonate melt serving as its own reaction. medium. When diphenyl carbonate is employed, there will be formed in the reaction medium a certain level of phenol which has proved to be an undesirable by-product. Therefore, subsequent to transesterification, it is advantageous to remove phenol through an alkali extraction wash or further react the phenol by the addition of acetic anhydride. This results in formation of phenylacetate and acetic acid along with the other components of the mixture. Where group B is phenyl, sulfonation of the phenyl is best achieved through the aforesaid removal of phenol and reaction with sulfur trioxide.

DETAILED DESCRIPTION

It has been found that quaternary ammonium functionalized alcohols readily undergo transesterification with low molecular weight carbonates to provide bleach precursors of Formula I. These products are described by the general formula:

$$A-O-\overset{O}{\underset{\|}{C}}-O-B \quad (I)$$

wherein:
A is $Z^-$

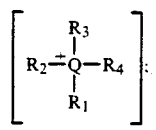

$R_1$, $R_2$ and $R_3$ are each a radical selected from the group consisting of alkyl, alkenyl, alkynyl, cycloalkyl, cycloalkenyl, aryl, hydroxyalkyl, polyoxyalkylene, and $R_4OC(O)OL$;
or $R_1$ and $R_2$ together form an alkyl substituted or unsubstituted nitrogen-containing heterocyclic ring system;
or at least one of $R_1$ and $R_2$ is attached to $R_4$ to form an alkyl substituted or unsubstituted nitrogen-containing heterocyclic ring system;

$R_4$ is selected form a bridging group consisting of alkylene, cycloalkylene, alkylenephenylene, arylene, and polyalkoxylene, and wherein the bridging group can be unsubstituted or substituted with $C_1-C_{20}$ atoms selected from alkyl, alkenyl, benzyl, aryl radicals;

$Z^-$ is a monovalent or multivalent anion leading to charge neutrality when combined with $Q^+$ in the appropriate ratio and wherein $Z^-$ is sufficiently oxidatively stable not to interfere significantly with bleaching by a peroxy carbonic acid;

Q is nitrogen or phosphorous;

B is A, $R_1$ or L; and

L is selected from the group consisting of:

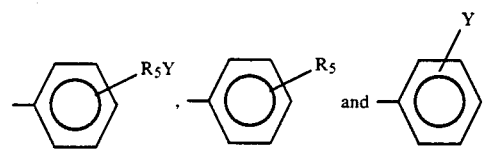

wherein $R_5$ is a $C_1-C_{12}$ alkyl group, and Y is H or a water solubilizing unit selected from the group consisting of $-SO_3^-M^+$, $-COO^-M^+$, $-SO_2^-M^+$, $-N^+(R_5)_3X^-$, $-NO_2$, $-OH$, and $-N(O)(R_5)_2$ and mixtures thereof; $M^+$ is a cation which provides solubility to the ester, and $X^-$ is an anion which provides solubility to the ester.

Most preferred of the leaving groups is the sulfonated phenol type. Especially useful is the 4-sulfophenol group. Sodium, potassium and ammonium cations are the preferred counterions to the sulfophenol structures.

In particular, it is desirable that $R_3$ be a short-chain $C_1-C_4$ alkyl radical, preferably methyl, while $R_1$ and $R_2$ may be a longer chain $C_7-C_{20}$ alkyl or alkylaryl, such as a stearyl, lauryl, or benzyl group. With regard to the $R_4$ bridge between the quaternary nitrogen and carbonate groups, it is desirable that $R_4$ be a bridging group selected from $C_2-C_{20}$ alkylene, $C_6-C_{12}$ phenylene, $C_5-C_{20}$ cycloalkylene, and $C_8-C_{20}$ alkylenephenylene groups. Preferably, the alkylene groups should have 2 carbon atoms. Further, the bridging group can be unsubstituted or substituted with $C_1-C_{20}$ alkyl, alkenyl, benzyl and aryl radicals.

Within the context of this invention, there may be compounds having the general structure (I) where $R_1$ and $R_4$ together or $R_1$ and $R_2$ together form an alkyl substituted or unsubstituted nitrogen-containing heterocyclic ring system. Representative of these systems are rings defining pyridine, morpholine, pyrrole, imidazole, triazole, tetrazole, pyrrolidine, piperidine and piperazine.

More specific compounds are listed in U.S. Pat. No. 4,751,015 which is herein incorporated by reference.

Generally the process comprises the steps of:
(i) forming an ester by transesterifying a hydroxyl compound of the formula:

with a carbonate ester of the formula:

wherein $R_8$ is selected from a substituted or unsubstituted phenyl, $C_1$–$C_{20}$ alkyl and mixtures of radicals thereof; and (ii) reacting the transesterified ester with $R_3Z$ to form the quaternary ammonium carbonate ester, $R_3$ being a $C_1$–$C_4$ alkyl group and Z being the same as $Z^-$ except without charge.

A variety of reactant $R_8OC(O)OR_8$ carbonate esters may be employed in the process of this invention. Advantageously, the $R_8$ radical is a phenyl.

Hydroxyl compounds especially suitable for this process are the N,N-dialkylaminoalkanols. Particularly preferred is N,N-dimethylaminoethanol. Replacement of choline chloride with N,N-dimethylaminoethanol more than doubles conversion of the diphenyl carbonate to the asymmetric carbonate. When N,N-dialkylaminoalkanols are used, no additional catalyst is required for the reaction.

Transesterification of the hydroxyl compound with carbonate ester may be conducted in an aprotic solvent media. Examples of such solvents include acetonitrile, nitrobenzene, nitroethane, nitrotoluene, toluene, benzene, dimethylsulfoxide and dimethylformamide. Most preferred is acetonitrile. Best results are, however, obtained by employing a melt of the carbonate ester as its own reaction media.

Normally solventless reactions are run at temperatures above the melting point of any reactants. For example, diphenyl carbonate when employed as reactant can serve as solvent at temperatures above 90° C., its melting point. Conversely, room temperature reactions usually require the presence of a separate solvent component. Reaction times can be decreased by greater than ten-fold in a carbonate melt compared to a solvent based reaction. Moreover, the resultant ester mixture may contain a higher percentage of the desired asymmetric carbonate than obtained with solvent systems.

Quaternization follows the transesterification step. Therein a compound of the formula $R_6Z$ is combined with the transesterified ester to achieve alkylation of the amino function. Methylation is the preferred form of quaternization. Suitable methylating agents are the methyl halides and methyl sulfate. Particularly preferred is methyl chloride.

A solvent may be employed for the quaternization reaction. Reaction rate can be quite dependent upon the choice of solvent. Preferably the solvent is an aprotic one. Solvents within the aprotic category include acetonitrile, acetone, ethers, toluene and $C_4$–$C_{20}$ hydrocarbons. Reaction rates in acetonitrile were found to proceed much faster than with toluene.

Quaternization may also be conducted in the absence of solvent using an excess of the methylating agent. For instance, methyl chloride can serve as its own solvent. Unreacted methyl chloride can, at the end of the reaction, be evaporated or recycled for use in a further batch.

A particularly preferred product derived from the transesterification-quaternization scheme is cholylphenylcarbonate (CPC) which arises from transesterification of diphenylcarbonate (DPC) with N,N-dimethylaminoethanol (DMAE) followed by quaternization with methyl chloride. Separation of the desired CPC from unreacted DPC and ester by-products can be difficult. Phenol has been identified as a constituent of the reaction mixture that hinders the isolation process. Extraction of phenol is conducted subsequent to the transesterification, but prior to quaternization.

Another way to remove the phenol by-product entails adding an equivalent of acetic anhydride to the transesterified mixture at elevated temperatures. The acetic anhydride rapidly reacts with phenol to form phenylacetate and acetic acid. Phenylacetate is a bleach precursor itself; therefore, the addition of acetic anhydride turns the undesired by-product, phenol, into a useful added ingredient and eliminates a costly extraction step.

An especially useful end-product of the process hereinabove described, is that of structure (I) where OB is a phenol sulfonate. Particularly preferred is 2-(N,N,N-trimethylammonium) ethyl 4-sulfophenyl carbonate (CSPC). The CSPC product may be derived from CPC through the further step of a sulfonation reaction. Liquid sulfur trioxide is the preferred reagent to accomplish sulfonation of the phenyl ring.

The following Examples will more fully illustrate the embodiments of this invention. All parts, percentages and proportions referred to herein and in the appended claims are by weight unless otherwise illustrated.

EXAMPLE I

Preparation of CSPC Via Transesterification

Transesterification

Into a 250 ml, three-necked round bottomed flask equipped with an overhead stirrer and placed in an oil bath was added (18.43 g, 0.086 mole) diphenylcarbonate. The oil bath was heated to 95° C. and the diphenylcarbonate was allowed to melt. N,N-dimethylaminoethanol (7.66, 0.086 mole) was added slowly dropwise over fifteen minutes with continued stirring, and the reaction was heated and stirred for an additional 15–30 minutes. $^1$H FTNMR of the amber liquid product in acetonitrile-$d_3$ indicated a 75:25 mixture of N,N-(dimethylamino)ethylphenylcarbonate and bis(N,N-dimethylamino)ethylcarbonate and showed the following peaks: δ 6.75–7.55 m; 4.25 (t, 2H); 4.15 (t, 2H); 2.6 (t, 2H); 2.5 (t, 2H); 2.25 (s, 6H); 2.15 (s, 6H). The more downfield shift of each pair of triplets and singlets corresponds to the monosubstituted carbonate. Phenol and unreacted diphenylcarbonate were also present in the mixture as by-products. The yield was 24 g.

Phenol Extraction

A 10.0 g portion of the mixture was dissolved in 75 ml $CHCl_3$ and extracted with 100 ml 5% NaOH in a separatory funnel for several minutes. Evaporation of the chloroform yielded a yellow liquid that was shown by HPLC to be 62.4% N,N-(dimethylamino)ethyl-phenylcarbonate, 24.6% diphenylcarbonate, 12.1% bis(N,N-dimethylamino)ethylcarbonate and 0.9% phenol by weight. The sample contained 31.5% phenol by weight before extraction. The yield was 5 g after extraction.

Quaternization with Methyl Chloride

The 5.0 g sample isolated after the phenol extraction was dissolved in 100 ml acetonitrile. Methyl chloride was then bubbled into the solution at 20 psi for one hour. The solution was chilled in an ice bath during the addition of methyl chloride but was left open to the atmosphere. Thereafter, the resultant opaque solution was rotary evaporated to dryness after warming to room temperature. A yield of 5.8 g was obtained. The $^1$H FTNMR indicated a mixture of N,N,N-(trimethylammonium)ethylphenylcarbonate chloride, bis- (N,N,N-trimethylammonium)ethylcarbonate dichloride, diphenylcarbonate and a small amount of phenol. Titration for chloride anion was then carried out with $AgNO_3$.

Sulfonation with Liquid $SO_3$

After quaternization the white solid product obtained therefrom was suspended in 50 ml chilled methylene chloride in a 250 ml round bottomed flask equipped with an overhead stirrer. $SO_3$ (2.5 ml, 0.062 mol) was added all at once and the reaction was stirred in an ice bath for several hours. A product precipitated as a thick beige colored liquid. Workup consisted of decanting the methylene chloride and dissolving the beige liquid in a minimum of water while chilling in an ice bath. Solid $CaCO_3$ was added slowly until the pH of the aqueous solution was about six. The solution was kept slightly acidic to prevent hydrolysis of the carbonate. After filtration of calcium salts, the solution was rotary evaporated to dryness. The yield was 6.0 g. $^1H$ FTNMR in $D_2O$ indicated CSPC, sulfonated diphenylcarbonate (SDPhC), bis(N,N,N-trimethylammonium)ethylcarbonate (TMAEC), and a small amount of phenolsulfonate (PS), and showed the following peaks: δ 7.75 (d, 4H, SDPhC); 7.7 (d, 2H, CSPC); 7.55 (d, 2H, PS); 7.3 (d, 4H, SDPhC); 7.2 (d, 2H, CSPC); 6.8 ((d, 2H, PS); 4.55 (m, 2H, CSPC and TMAEC); 3.6 (m, 2H, CSPC and TMAEC); 3.0 (s, 9H, CSPC and TMAEC).

EXAMPLE II

Preparation of CSPC with Excess Diphenylcarbonate

Transesterification

Into a 500 ml, three-necked round bottomed flask equipped with an overhead stirrer and placed in an oil bath was added diphenylcarbonate (75 g, 0.347 mole). The oil bath was heated to 90°-100° C. and the diphenylcarbonate was allowed to melt. N,N-dimethylaminoethanol (3.09 g, 0.0347 mole) was added dropwise to the stirred 10-fold excess diphenylcarbonate melt. Thereafter, the reaction was heated and additionally stirred for 20-30 minutes. $^1H$ FTNMR of the amber liquid product in acetonitrile-$d_3$ indicated a 95:5 mixture of N,N-(dimethylamino)ethylphenylcarbonate (DMAEC) and bis-(N,N-dimethylamino)ethylcarbonate (DMAEC) and showed the following peaks: δ 6.75-7.55 (m, aryl peaks); 4.25 (t, 2H, DMAEPC); 4.15 (t, 2H DMAEC); 2.60 (t, 2H DMAEPC); 2.50 (t, 2H DMAEC); 2.25 (s, 6H DMAEPC); 2.15 (s, 6H DMAEC). Phenol and unreacted diphenylcarbonate were also present in the mixture as by-products.

Phenol Extraction and Quaternization

Phenol extraction with aqueous base and quaternization in $CH_3Cl$ were performed as described in Example I. The final product mixture contained <1% phenol along with the quaternized N,N,N-(trimethylammonium)ethylyphenylcarbonate chloride, bis-(N,N,N-trimethylammonium)ethylcarbonate dichloride and a large amount of excess, unreacted diphenylcarbonate.

Toluene Extraction of Diphenylcarbonate

The quaternized mixture was suspended in 250 ml of toluene and stirred vigorously for one hour. Then the suspension was filtered and washed several times with diethyl ether. Diphenylcarbonate remained in the toluene filtrate and the quaternized, insoluble N,N,N-(trimethylammonium)ethylphenylcarbonate chloride and bis-(N,N,N-trimethylammonium)ethylcarbonate dichloride were filtered out of solution and extracted from the diphenylcarbonate. Quaternized product was isolated in the amount of 8.46 g (90% yield). Separation by HPLC showed the presence of <1% phenol and no diphenylcarbonate.

Sulfonation with Liquid $SO_3$

The sulfonation of the quaternized mixture (8.36 g) was performed as described in Example I using liquid $SO_3$ (5.1 g, 2.6 ml). The sulfonated mixture was neutralized with calcium carbonate and isolated as a white solid with 60-65% CSPC activity.

EXAMPLE III

Preparation of CSPC Using Acetic Anhydride to Remove Phenol

Transesterification

The transesterification reaction was performed as described in Example I using N,N-dimethylaminoethanol (7.66 g, 0.086 mole) and diphenylcarbonate (18.43 g, 0.086 mole). The product mixture again contained N,N-(dimethylamino)ethylphenylcarbonate, bis(N,N-dimethylamino)ethylcarbonate, diphenylcarbonate and phenol.

Addition of Acetic Anhydride

To the transesterification melt (after 30-45 minutes reaction) was added acetic anhydride (8.77 g, 0.086 mole) and the mixture was stirred at 90°-100° C. for 2 hours until the reaction with phenol was complete. The mixture was cooled to room temperature and an amber liquid resulted. $^1H$ NMR of this mixture in $CD_3CN$ indicated removal of phenol and formation of phenylacetate and acetic acid and showed the following peaks: δ 7.0-7.6 m (aryl peaks); 2.32 s ($CH_3$—phenylacetate); 2.05 s ($CH_3$—acetic acid). The NMR also showed the presence of the remaining N,N-(dimethylamino)ethylphenylcarbonate, diphenylcarbonate, and bis(N,N-dimethylamino)ethylcarbonate.

Quaternization and Sulfonation

The quaternization with $CH_3Cl$ and sulfonation with $SO_3$ were carried out as reported in Example I. An equivalent of $SO_3$ was added for every phenyl substituent and every chloride anion present. After neutralization with $CaCO_3$ and lyophilization, a white solid was isolated. $^1H$ NMR of the solid in $D_2O$ indicated sulfonation had occurred and showed the presence of CSPC, sulfonated diphenylcarbonate (SDPhC), bis(N,N,N-trimethylammonium)ethylcarbonate dichloride (TMAEC), sodium acetyloxybenzenesulfonate (SABS) and sodium acetate (SA) with the following peaks: δ 7.95 (d, 4H, SDPhC); 7.8 (d, 2H, CSPC); 7.75 (d,2H,SABS); 7.48 (d, 4H, SDPhC); 7.40 (d, 2H, CSPC); 7.35 (d, 2H, SABS); 4.8 (m, 2H, CSPC and TMAEC); 3.82 (m, 2H, CSPC and TMAEC); 3.28 (s, 9H, CSPC and TMAEC); 2.4 (s, 3H, SABS); 2.0 (s, 3H, SA). The HPLC of the final product indicated 61% active materials (31% CSPC and 30% SABS).

EXAMPLE IV

Bleaching Results with CSPC Prepared Via Transesterification

Bleaching studies with the precursor CSPC were carried out on tea-stained cloths at several temperatures and at different active oxygen to precursor levels. A typical experiment was carried out as follows:

Sodium perborate and precursor were added to a one liter terg-o-tometer pot containing detergent and test cloths heated to the desired temperature. The cloths were agitated for 15 minutes, while the pH of the wash liquor was adjusted to ten and maintained there for the entire wash. The cloths were then rinsed with tap water, dried in a microwave oven and the change in reflectance measured on a Hunterlab Colorgard/05 tristimulus colorimeter. Change in reflectance was measured before and after the cloths were washed. Performance data is represented as the change in the Y tristimulus value, which is the change in reflectance of the cloth over a range of wavelengths centered in the visible portion of the electromagnetic spectrum. Blanks were run in the same manner but without precursor. $\Delta\Delta R$ values are reported as the difference in reflectance between the experimental and blank runs for each set of conditions.

| Temperature | Perborate:Precursor | $\Delta\Delta R$ |
|---|---|---|
| 40° C. | 3:1 | 17.5;17.4 |
|  | 5:1 | 17.3;17.3 |
|  | 8:1 | 17.5;17.8 |
| 30° C. | 3:1 | 13.7 |
|  | 5:1 | 14.2 |
|  | 8:1 | 13.6 |
| 20° C. | 3:1 | 9.3 |
|  | 5:1 | 9.5 |
|  | 8:1 | 9.2 |

Conditions: 1.75 g/L (P-SURF ®), 10 ppm AOX precursor, perborate monohydrate, 0 ppm hardness, 15 minute wash, one liter terg, pH = 10.00.

The foregoing description and examples illustrate selected embodiments of the present invention. In light thereof, various modifications will be suggested to one skilled in the art, all of which are within the spirit and purview of this invention.

What is claimed is:

1. A process is provided for the preparation of quaternary ammonium carbonate esters of the formula:

$$A-O-\overset{O}{\underset{\|}{C}}-O-B \quad (I)$$

wherein:

A is $Z^-$

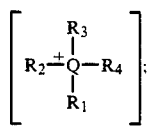

$R_1$ and $R_2$ are each a radical selected from the group consisting of alkyl, alkenyl, alkynyl, cycloalkyl, cycloalkenyl, aryl, hydroxyalkyl, polyoxyalkylene, and $R_4OC(O)OL$;

$R_4$ is selected from a bridging group consisting of alkylene, cycloalkylene, arylene, and polyakloxylene, and wherein the bridging group can be unsubstituted or substituted with $C_1-C_{20}$ atoms selected from the group consisting of alkyl, alkenyl, benzyl and aryl radicals;

$Z^-$ is a monovalent or multivalent anion leading to charge neutrality when combined with $Q^+$ in the appropriate ratio and wherein $Z^-$ is sufficiently oxidatively stable not to interfere significantly with bleaching by a peroxy carbonic acid;

Q is nitrogen or phosphorus;

B is $R_1$ or L; and

L is selected from the group consisting of:

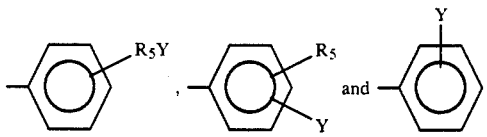

wherein $R_5$ is a $C_1-C_{12}$ alkyl group, and Y is H or a water solubilizing unit selected from the group consisting of $-SO_3^-M^+$, $-COO^-M^+$, $-SO_2^-M^+$, $-N^+(R_5)_3X^-$, $-NO_2$, $-OH$, and $-N(O)(R_5)_2$ and mixtures thereof; $M^+$ is a cation which provides solubility to the ester, and $X^-$ is an anion which provides solubility to the ester comprising the steps of:

(i) forming an ester by transesterifying a hydroxyl compound of the formula:

$$R_2-\overset{R_1}{\underset{|}{Q}}-R_4-OH \quad (II)$$

with $R_8OC(O)OR_8$ wherein $R_8$ is a radical selected from the group consisting of substituted or unsubstituted phenyl, $C_1-C_{20}$ alkyl, and mixtures of radicals thereof; and (ii) reacting said transesterified ester with $R_3Z$ to form said quaternary ammonium carbonate ester, $R_3$ being a $C_1-C_4$ alkyl group and Z being the same as $Z^-$ except without charge.

2. A process according to claim 1 wherein $R_8$ is phenyl.

3. A process according to claim 2 further comprising the steps of removing phenol from products resulting from the transesterification step, said removal being prior to reacting said hydroxyl compound with $R_3Z$.

4. A process according to claim 1 wherein transesterification is performed in an aprotic solvent.

5. A process according to claim 1 wherein the carbonate ester product is 2-(N,N,N-trimethylammonium)ethyl 4-sulfophenyl carbonate.

6. A process according to claim 1 further comprising sulfonating the quaternary ammonium carbonate ester resulting from step (ii).

7. A process according to claim 6 wherein said sulfonation is conducted through use of sulfur trioxide.

8. A process according to claim 1 wherein transesterification is conducted in the absence of a solvent.

9. A process according to claim 1 wherein said transesterification step is conducted in the presence of an excess amount beyond that necessary for reaction of $R_8OC(O)OR_8$.

10. A process according to claim 1 wherein said hydroxyl compound is an N,N-dialkylaminoalkanol.

11. A process according to claim 10 wherein said hydroxyl compound is N,N-dimethylaminoethanol.

12. A process according to claim 1 wherein $R_3Z$ is selected from the group consisting of methyl chloride and methyl sulfate.

13. A process according to claim 3 wherein the phenol is removed by extraction with an aqueous base solution.

14. A process according to claim 3 wherein the phenol is removed by further reaction of product arising from the transesterification step with acetic anhydride.

* * * * *